United States Patent [19]

Müller et al.

[11] Patent Number: 4,705,679

[45] Date of Patent: Nov. 10, 1987

[54] TRANSPARENT DENTAL CARE COMPOSITION

[75] Inventors: Karl-Hans Müller, Bruchköbel; Matthias Neumüller, Hasselroth; Günther Türk, Hanau, all of Fed. Rep. of Germany

[73] Assignee: Degussa Aktiengesellschaft, Frankfurt, Fed. Rep. of Germany

[21] Appl. No.: 7,214

[22] Filed: Jan. 27, 1987

Related U.S. Application Data

[60] Division of Ser. No. 773,973, Sep. 9, 1985, Pat. No. 4,664,907, which is a continuation of Ser. No. 641,812, Aug. 17, 1984, abandoned, which is a continuation of Ser. No. 510,452, Jul. 1, 1983, abandoned, which is a continuation of Ser. No. 364,035, Mar. 31, 1982, abandoned.

[30] Foreign Application Priority Data

Apr. 10, 1981 [DE] Fed. Rep. of Germany ....... 3114492

[51] Int. Cl.$^4$ .......................... A61K 7/16; A61K 7/18
[52] U.S. Cl. ......................................... 424/52; 424/49
[58] Field of Search ..................................... 424/49–58

[56] References Cited

U.S. PATENT DOCUMENTS

| | | | |
|---|---|---|---|
| 3,538,230 | 11/1970 | Pader et al. | 424/49 |
| 3,705,940 | 12/1972 | Kirchgassnor | 424/49 |
| 3,840,657 | 10/1974 | Norfleet | 424/49 |
| 3,864,470 | 2/1975 | Watson | 424/49 |
| 3,934,000 | 1/1976 | Bakth | 424/49 |
| 4,105,757 | 8/1978 | Wason | 424/49 |
| 4,132,806 | 1/1979 | Wason | 424/49 |
| 4,156,717 | 5/1979 | Wason | 424/49 |
| 4,294,894 | 10/1981 | Vellucci | 424/49 |
| 4,305,928 | 12/1981 | Harvey | 424/49 |
| 4,314,990 | 2/1982 | Denny et al. | 424/49 |
| 4,332,791 | 6/1982 | Raaf et al. | 424/49 |
| 4,336,245 | 6/1982 | Wason | 424/49 |
| 4,356,168 | 10/1982 | Harvey et al. | 424/49 |

FOREIGN PATENT DOCUMENTS

| | | |
|---|---|---|
| 1241877 | 8/1971 | United Kingdom . |
| 1263945 | 2/1972 | United Kingdom . |
| 1372663 | 11/1974 | United Kingdom . |
| 1400793 | 7/1975 | United Kingdom . |
| 1433743 | 4/1976 | United Kingdom . |
| 1536199 | 12/1978 | United Kingdom . |

*Primary Examiner*—Shep K. Rose
*Attorney, Agent, or Firm*—Beveridge, DeGrandi & Weilacher

[57] ABSTRACT

Figure 1:
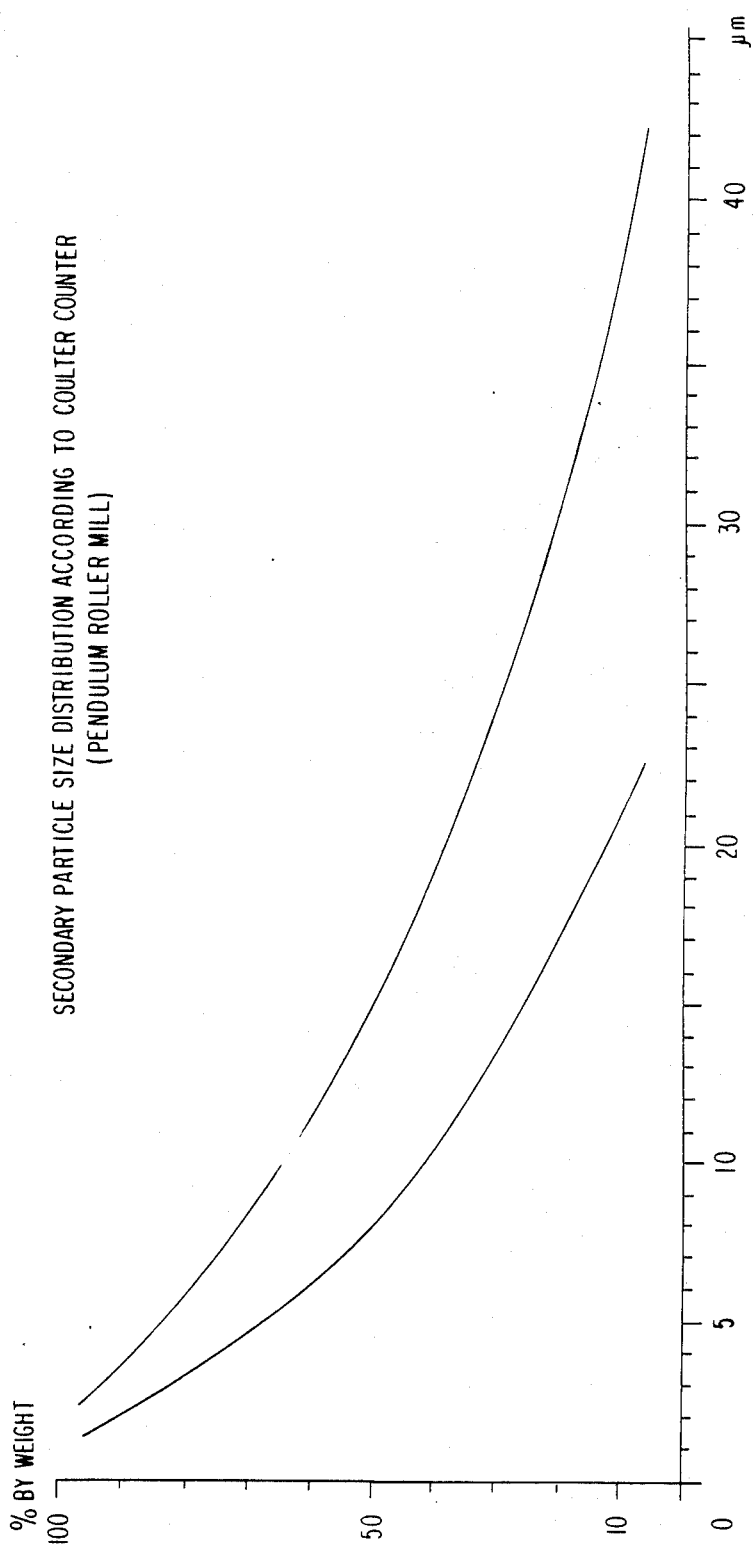
Figure 2:
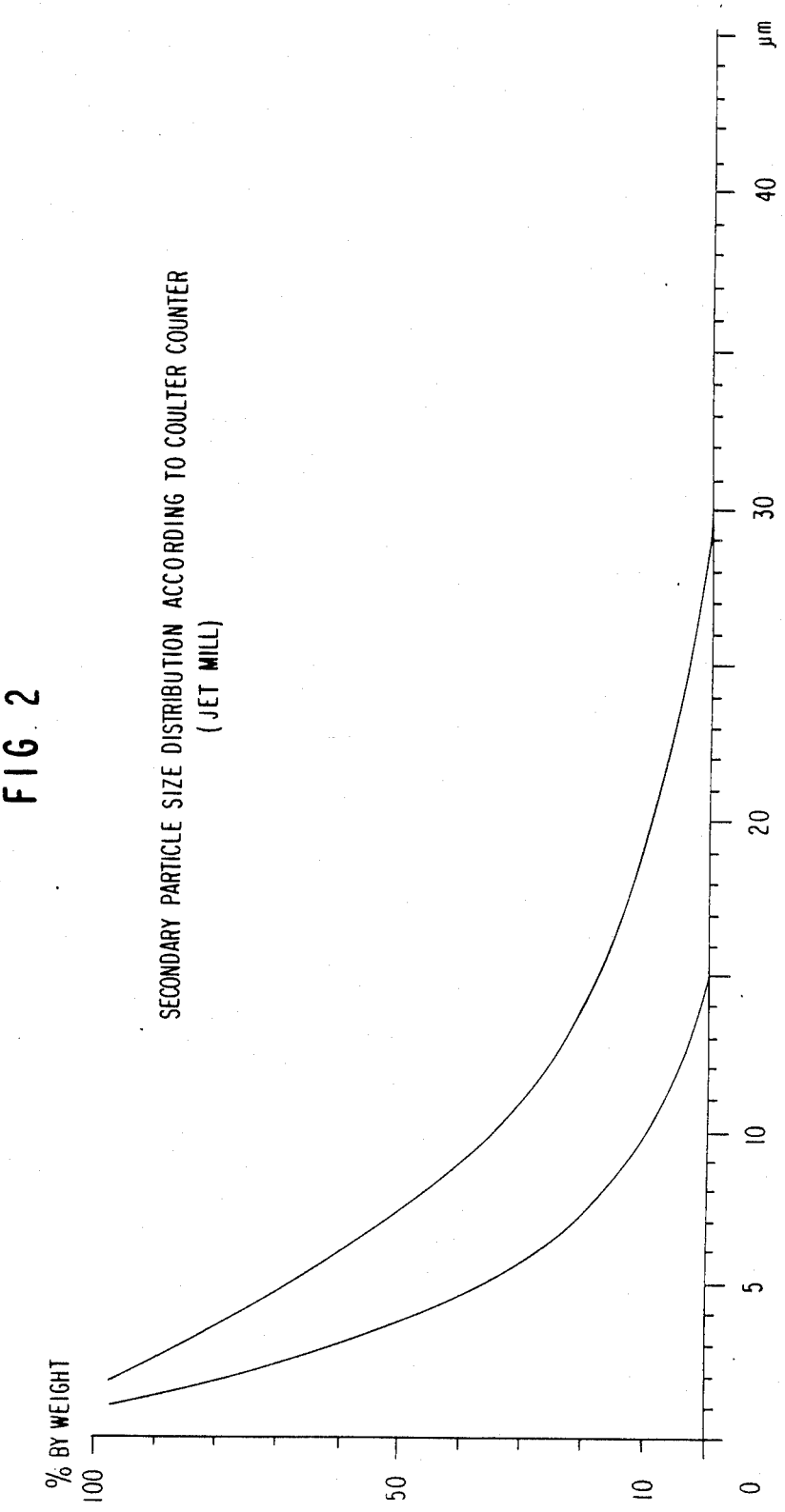

A dental-care composition having improved shelf life in respect of rheology and abrasiveness, which, as a novel feature, contains, as a cleansing agent, a bifunctional (thickening and abrasive) precipitated silica characterized by the following physico-chemical properties:

| | | Pendulum roller mill | Jet mill |
|---|---|---|---|
| BET surface area | m$^2$/g | 15–110 | 15–110 |
| Tamped density | g/l | 150–750 | 90–650 |
| Secondary particle size distribution according to Coulter Counter | | FIG. 1 | FIG. 2 |
| "ALPINE" screen retainings >63 µm | % by weight | <1.5 | <0.1 |
| Cu abrasion in 10% strength glycerol dispersion | mg | 5–30 | 5–30 |
| Lightness value A | % | 86–96 | 90–96 |
| Viscosity in a 30% strength dispersion in a 1:1 glycerol/water mixture, Brookfield RTV, Sp5 | | 30,000–60,000 | 30,000–60,000 |

The dental-care composition may additionally contain 0.5–5% by weight of polyethylene glycol or 2–14% by weight of a precipitated silica which in 15% strength dispersion in a glycerol/water mixture has a viscosity of not less than 30,000 mPa.s. Pyrogenic silica can also be employed successfully to regulate the viscosity of the product.

19 Claims, 4 Drawing Figures

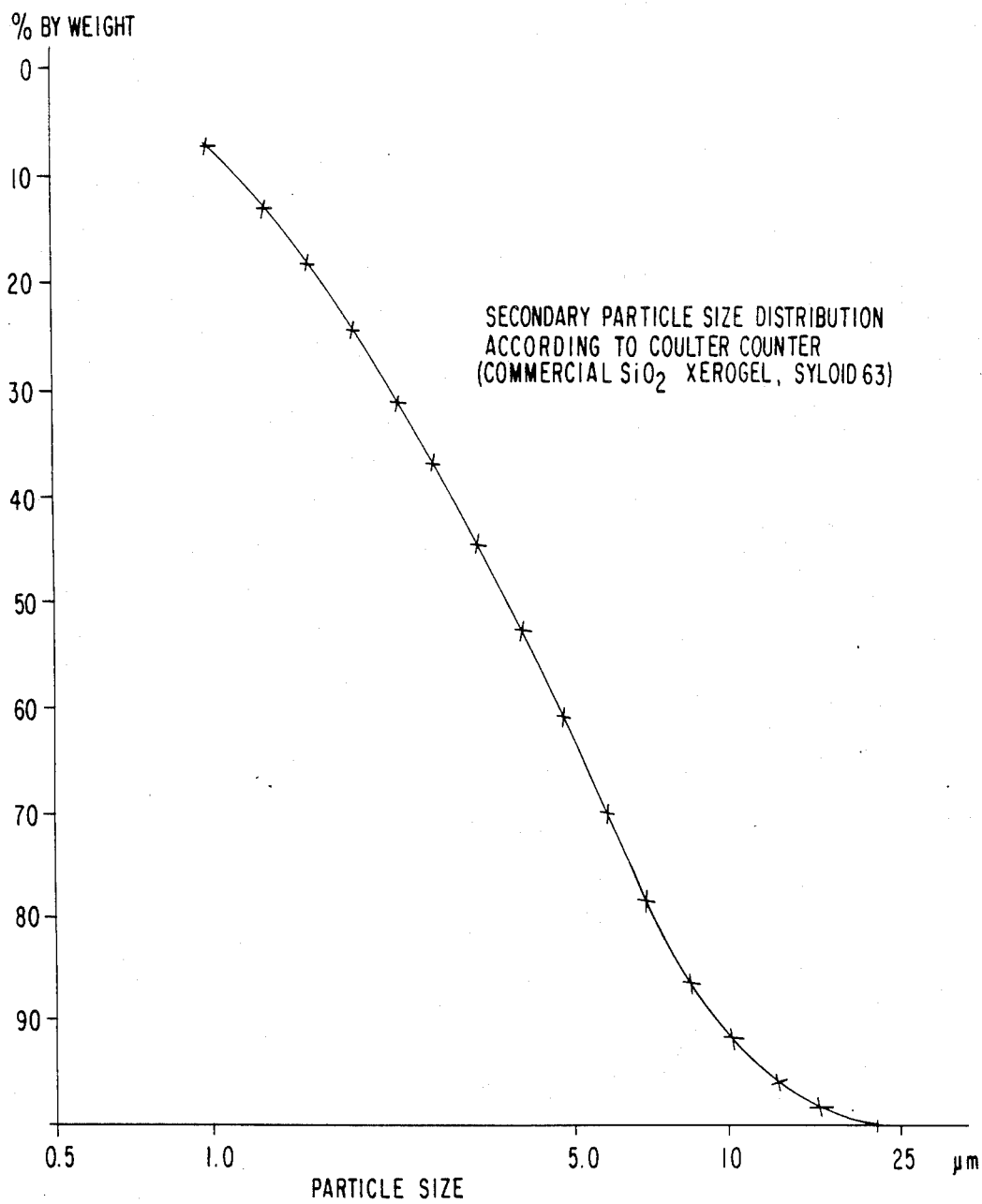

TRANSPARENT DENTAL CARE COMPOSITION

REFERENCE TO A RELATED APPLICATIONS

This application is a division of our copending application Ser. No. 773,973 filed Sept. 9, 1985, now U.S. Pat. No. 4,664,907, which in turn is a continuation of copending application Ser. No. 641,812 filed Aug. 17, 1984, abandoned, which in turn is a continuation of copending application Ser. No. 510,452 filed July 1, 1983, abandoned, which in turn is a continuation of copending application Ser. No. 364,035 filed Mar. 31, 1982, abandoned, and all relied on.

It is known that amorphous synthetic silicas may be used as cleansing agents in toothpastes. Silicas, used as cleansing agents, have the vital advantage over the previously used calcium phosphates and chalks that they do not react with the fluoride ions frequently employed in the form of tin(II) fluoride and sodium fluoride as anti-caries agents, and thus do not block the effect of these additives.

Accordingly, there is a need to replace the cleansing agents based on calcium phosphates and chalks by an inert substance.

A first vital successful step in this direction was the introduction of amorphous high porous silica xerogels (U.S. Pat. No. 3,538,230), the combination of which with thickening aerogels, for example Syloid 244 ®, finally allowed the commercial breakthrough of the use of silica gels in toothpastes. However, it must be pointed out that use had been made much earlier of the viscosity-regulating effect of certain silicas, for example pyrogenic and precipitated silicas having a high degree of structure (German Pat. No. 1,667,875 corresponding to U.S. Pat. No. 3,705,940 and British Pat. No. 1,241,877). In subsequent development, the combination of cleansing agents based on silica xerogels with pyrogenic silicas (German Published Application DAS No. 2,033,678 corresponding to U.S. Pat. No. 3,689,637 and British Pat. No. 1,298,130) and with thickening precipitated silicas having a medium to high degree of structure (British Pat. No. 1,433,743, German Published Application DAS No. 2,610,207 and U.S. Pat. No. 4,132,806) was, logically, also pursued.

The next step with regard to the production of improved novel cleansing agents was the development of a specific aluminum silicate produced by precipitation, and the combination of this silicate with a thickening pyrogenic silica or with a thickening precipitated silica of medium to high degree of structure is described in German Pat. No. 2,154,376 corresponding to British Pat. No. 1,400,793 and German Published Application DAS No. 2,206,285 corresponding to British Pat. No. 1,372,663.

Subsequent development next led to cleansing agents based on precipitated silicas which produced no significant thickening action but had markedly lower abrasiveness than the calcium phosphate cleansing agents. Where these novel $SiO_2$-based precipitated silicas are used, the rheology of the toothpastes is not regulated by means of thickening precipitated silicas, but by addition of special binders such as seaweed colloids or synthetic cellulose derivatives (carragheen and sodium carboxymethylcellulose) and by means of vegetable gums (German Laid-Open Application DOS No. 2,344,316; U.S. Pat. No. 4,105,757; German Laid-Open Application DOS No. 2,344,805; U.S. Pat. Nos. 4,122,160 and 4,144,321, and German Laid-Open Application DOS No. 2,522,486 corresponding to U.S. Pat. Nos. 4,067,746 and 4,191,742).

Nowadays, a modern cleansing agent based on silicas and intended for use in toothpastes has to provide the following effects:

reduced abrasiveness, in the sense of medium polishing activity (Cu abrasion in the finished toothpaste, between 8 and 14 mg), in order to protect the dental enamel, at filler contents in the range of 15–25% by weight, based on the amount of one and the same bifunctional cleansing agent (producing both abrasion and thickening), the viscosity, under conditions which give the above Cu abrasion range, should be between 2,500 and 4,500 mPa.s (determined by the Rotovisko-PK method), the ribbon of toothpaste leaving the tube should be smooth, glossy and free from specks and the dental-care composition containing the cleansing agent should have improved shelf life, in the sense of exhibiting constant abrasiveness and degree of thickening (no after-thickening) for a period of at least one year.

It is an object of the invention to conform to the above requirements of a dental-care composition by choice and use of a suitable cleansing agent.

We have found that this object is achieved as follows:

We resort to a process for the preparation of precipitated silicas which, depending on the manner in which they are milled, gives precipitated silicas having the following physico-chemical characteristics:

| | | Pendulum roller mill | Jet mill |
|---|---|---|---|
| BET surface area determined according to DIN 66,131 | m²/g | 15–110 | 15–110 |
| Tamped density determined according to DIN 53,194 | g/l | 150–750 | 90–650 |
| Cu abrasion in 10% strength glycerol dispersion | mg | 5–30 | 5–30 |
| Viscosity of a 30% strength dispersion in a 1:1 glycerol/water mixture (Brookfield RTV, Sp5) | mPa · s | 30,000 to 60,000 | |
| Lightness value A according to DIN 55,921 | % | 86–96 | 90–96 |
| Secondary particle size distribution curve according to Coulter counter | | according to FIG. 1 | according to FIG. 2 |
| "ALPINE" screen retainings >63 μm | % by weight | <1.5 | <0.1 |

Such precipitated silicas are very particularly suitable for use in the novel dental-care compositions which are intended to exhibit the pattern of properties referred to above.

The process for the preparation of precipitated silicas having the above pattern of properties is characterized in that an original precipitated silica suspension, which is prepared by precipitating the silica in an initial charge of alkali metal silicate solution, having a concentration of about 5–25 g of $SiO_2$ per liter of solution, by means of an acid and alkali metal silicate solution of particular concentrations, at particular feed rates, while maintaining a precipitation temperature in the reaction medium between 80° and 90° C., the precipitation being carried out under such conditions that the viscosity of the reaction medium is kept, for at least 30% of the total precipitation time, at a uniform low value while the pH is kept between 10 and 12, and the addition of the reactants only being terminated when the viscosity, after passing through a maximum, has dropped to a value which is less than 100% above the initial value, is diluted with hot water to a precipitated silica content of 10–30 g/l and a sodium sulfate content of 6–20 g/l, and heated to 85°–95° C., the pH is brought to 7–9 with sulfuric acid and, while keeping this pH value constant, alkali metal silicate solution, sulfuric acid and hot water are added simultaneously over a precipitation period of 30–180 minutes so as to give a final concentration of precipitated silica of 40–80 g/l, the suspension is acidified with concentrated sulfuric acid to a pH below 7, and the precipitated silica is separated from the suspension by means of a filter press, washed out, dried and milled by means of a pendulum roller mill or jet mill.

In a preferred embodiment, it is possible to use an original precipitated silica suspension which has been subjected to intensive shearing during its phase of preparation according to German Published Application DAS No. 1,467,019. This is of advantage whenever particularly high Cu abrasion values are to be achieved. In a particular embodiment of the invention, shearing can be effected according to German Pat. No. 1,767,332.

The present invention provides a dental-care composition having improved shelf life in respect of rheology and abrasiveness, which contains, as a thickener and abrasive, a precipitated silica characterized by the following physico-chemical properties:

| | | |
|---|---|---|
| BET surface area determined according to DIN 66,131 | m$^2$/g | 15–110 |
| Tamped density | g/l | 90–650 |
| Secondary particle size distribution curve according to Coulter counter | according to FIG. 2 | |
| "ALPINE" screen retainings >63 μm | % by weight | <0.1 |
| Cu abrasion in 10% strength glycerol dispersion | mg | 5–30 |
| Viscosity of a 30% strength dispersion in a 1:1 water/glycerol mixture (Brookfield RTV Sp 5) | mPa · s | 30,000–60,000 |
| Lightness value A according to DIN 55,921 | % | 90–96 |

The dental-care composition according to the invention exhibits the following advantageous properties:
it possesses mild abrasiveness, in the sense of medium polishing action on the surface of the teeth, without damaging the dental enamel,
if 15–25% by weight of cleansing agent, based on a single silica, are used, mild abrasion (8–14 mg Cu abrasion) coupled with optimum rheology of the paste (viscosity between 2,500 and 4,500 mPa.s determined by the Rotovisko method) can be achieved,
the ribbon of toothpaste is smooth, speck-free and glossy and
the toothpaste exhibits improved shelf life in respect of constancy of abrasiveness and thickening (without after-thickening).

The invention further provides a dental-care composition with improved shelf life in respect of rheology and abrasiveness, which contains, as the abrasive, a precipitated silica characterized by the following physicochemical properties:

| | | |
|---|---|---|
| BET surface area determined according to DIN 66,131 | m$^2$/g | 15–110 |
| Tamped density | g/l | 150–750 |
| Secondary particle size distribution according to FIG. 1 | | |
| "ALPINE" screen retainings >63 μm | % by weight | <1.5 |
| Cu abrasion in 10% strength glycerol dispersion | mg | 5–30 |
| Viscosity of a 30% strength dispersion in a 1:1 glycerol/water mixture (Brookfield RTV Sp5) | mPa · s | 30,000–60,000 |
| Lightness value A according to DIN 55,921 | % | 86–96 |

The dental-care composition according to the invention can have a total precipitated silica content of 17 to 25% by weight, preferably of 17 to 22% by weight. If the abrasive silica is used as the sole silica component, its concentration is 20 to 25% by weight, preferably 20 to 22% by weight. If mixtures of abrasive precipitated silica and thickening precipitated silica are employed, the following concentrations result: 15 to 20% by weight of abrasive precipitated silica 2 to 14% by weight, preferably 2 to 10% by weight, of thickening silica.

This novel dental-care composition has the following advantageous properties:
it possesses mild abrasiveness, in the sense of medium polishing action on the surface of the teeth, without damaging the dental enamel,
improved shelf life in respect of constant abrasiveness and thickening (without after-thickening) for a period of at least one year.

In a particular embodiment, 0.5–5% by weight of polyethylene glycol having a molecular weight in the range from 400 to 2,000 may be added, as a thickener, to the recipe of the dental-care composition. This measure has the effect of either reducing the amount of cleansing agent needed for a given final viscosity of the dental-care composition or of producing, at constant cleansing agent concentration, a higher viscosity of the toothpaste (for example, a different viscosity may be needed depending on whether the toothpaste is packed in a tube or a dispenser).

In a further embodiment, there may also be added to the toothpaste recipe 2–14% by weight, preferably 2–10% by weight, of a precipitated silica, available, for example, under the trademarks FK 320 DS, Sipernat 22 S ®, FK 300 DS, ZeoSil 200 or Sident 11 ®, which in 15% strength dispersion in a 1:1 glycerol/water mixture has a viscosity of not less than 30,000 mPa.s., or 0.5–4% by weight, preferably 2–4% by weight, of a pyrogenic silica which is available, for example, under the tradenames Aerosil 200 ®, Cabosil M5 ®, Aerosil 200 V ® or HDK N 20 E, together with cleansing agents, as thickener. In this way, the polishing action of the dental-care composition can be increased by using a silica cleansing agent which has a marked abrasive action but is in general a less effective thickener, if, at the same time, the reduction in thickening action is compensated by addition of precipitated silicas or pyrogenic silicas having an appropriate thickening action. This situation applies, for example, when formulating a smoker's toothpaste.

By combination of the SiO$_2$ cleansing agents, used in the novel dental-care composition, with thickening additives such as polyethylene glycol or pyrogenic or precipitated silica, the dental cosmetician is provided with means which allow him a substantial extension of the usefulness of the noveal dental-care compositions. At the same time it is to be borne in mind that these embodiments also have substantially improved properties in respect of shelf life of the composition.

Of course, the dental-care compositions according to the invention can be prepared either in a transparent or in an opaque form.

Principal constituents of transparent toothpastes:

water, glycerol and cleansing agent, the latter being silicon dioxide (silica).

Subsidiary constituents:

binders, eg. carboxymethylcellulose, preservatives (eg. sodium benzoate), sweetener (eg. saccharin), aromatic oils, foaming agents (eg. sulfonates), active ingredients, eg. fluorides, and dyes.

Principal constituents of opaque pastes:

cleansing agents, water and sorbitol.

In opaque pastes, the cleansing agents may also include chalks, aluminum hydroxides and calcium phosphates in addition to silicas and amorphous silicates (sodium aluminosilicates).

Subsidiary constituents:

binders (eg. carboxymethylcellulose), preservatives (eg. Na benzoate), sweetener (eg. saccharin), opacifiers (eg. $TiO_2$), active ingredients (eg. fluorides), foaming agents (eg. sulfonates) and, if desired, dyes.

The examples which follow illustrate and describe the novel dental-care compositions in comparison with prior art compositions.

The precipitated silicas, pyrogenic silicas and silica xerogels used to prepare the dental-care compositions are summarized in Survey Table No. 1 on page 12, together with those of their physico-chemical data which are considered relevant to their use in toothpastes. In the examples section, the letters A–I are employed in connection with the recipe and the description of the results. The letters A–D designate the abrasive silicas using in the dental-care composition according to the invention. In addition to the silica-containing toothpaste fillers listed in the table, the following fillers are used for comparative experiments: chalk ($CaCO_3$), produced by Schäfer, Diez/Lahn, West Germany. Dicalcium phosphate dihydrate, produced by Benckiser-Knapsack, West Germany. Titanium dioxide RN 56, produced by Kronos AG, West Germany.

All other toothpaste raw materials contained in the recipes given are listed in alphabetical order, together with information on suppliers, in Survey Table No. 2.

To demonstrate the technical effects, and for comparative investigations, essentially four basic recipes are used in the examples section, namely:

An opaque sorbitol paste which contains 40% by weight of sorbitol as the main constituent.

A transparent glycerol paste which contains 60% by weight of glycerol as the main constituent.

A chalk paste containing glycerol.

A phosphate paste containing sorbitol and glycerol.

The exact composition of the pastes investigated is in each case given in detail in the corresponding example sections. As a rule, an increase in the content of cleansing agent is compensated by a decrease in the water content.

To produce the pastes, the components are compounded in a RETSCH mill, homogenized three times on a triple-roll mill and then deaerated in a desiccator using a vacuum pump.

TABLE No. 1

Precipitated silicas, pyrogenic silicas and silica xerogels, the use of which in dental-care compositions is described in the examples.

Figure 3:
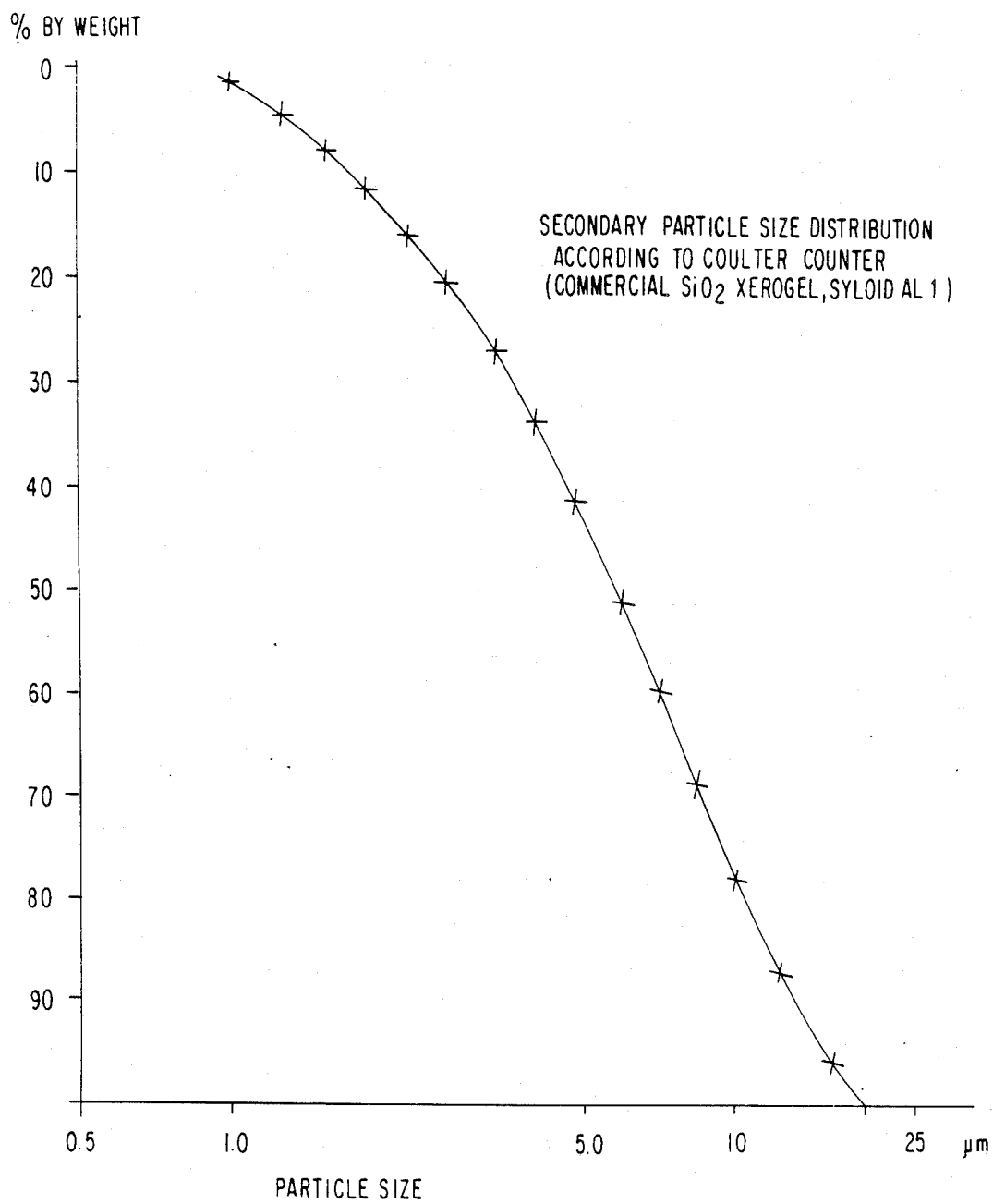

| Physico-chemical characteristics Type: | Abrasive silica A | Abrasive silica B | Abrasive silica C | Abrasive silica D | Commercial $SiO_2$ xerogel, Syloid ALi E | Commercial $SiO_2$ xerogel, Syloid 63 F | Commercial precipitated silica FK 320DS G | Commercial pyrogenic silica, Aerosil 200 V H | Commercial precipitated silica FK 300 DS I |
|---|---|---|---|---|---|---|---|---|---|
| BET surface area, $m^2/g$ | 103 | 101 | 70 | 51 | 633 | 719 | 170 | 200 | 300 |
| Secondary particle size distribution, according to Coulter Counter | FIG. 1 | FIG. 2 | FIG. 2 | FIG. 2 | FIG. 3 | FIG. 4 | FIG. 2 | — | FIG. 2 |
| "ALPINE" screen retainings >63 μm (% by weight) | 1.4 | 0.1 | 0.1 | 0.1 | <0.1 | <0.1 | — | — | — |
| Cu abrasion* (mg) | 14 | 8 | 12 | 17 | 7–8 | 11–12 | <1 mg | <1 mg | <1 mg |
| Viscosity** (mPa.s) | 36,000** | — | 38,400** | 33,500** | not measurable, too mobile | not measurable, too mobile | 52,200*** | — | 54,000*** |
| Lightness value A (%) | 94.4 | 96.8 | 95.7 | 94.6 | — | 94.1 | — | — | — |

*in 10% strength glycerol dispersion
**in 30% dispersion in a 1:1 glycerol/water mixture
***in 15% strength dispersion in a 1:1 glycerol/water mixture TABLE No. 2

Toothpaste raw materials and source of supply (excepting fillers)

| Raw material | Chemical name | Supplier company |
|---|---|---|
| aromatic oil | peppermint oil, oil of wintergreen | Haarmann and Reimer, Dragoco |
| Dehydazol A 400 P 0.5% strength dye solution | carboxymethylcellulose foodstuff dyes | Henkel Siegle-Farben |
| Glycerol | glycerol, German Pharmacopeia 7 | Merck |
| Polyethylene glycol 400 | polyethylene glycol | Merck |
| Polyethylene glycol 1500 | polyethylene glycol | Merck |
| liquid paraffin | paraffin | Merck |
| saccharin | benzoic acid sulfimide | Bayer |

TABLE No. 2-continued

Toothpaste raw materials and source of supply (excepting fillers)

| Raw material | Chemical name | Supplier company |
| --- | --- | --- |
| sodium saccharin | sodium salt of benzoic acid sulfimide | Bayer |
| Solbrol M | methyl p-hydroxybenzoate | Bayer |
| Solbrol M—Na | sodium salt of methyl p-hydroxybenzoate | Bayer |
| sorbitol | sorbitol | Maizena |
|  | Karion F (70% strength aqueous sugar solution) | Merck |
| Texapon K 12 | sodium laurylsulfonate | Henkel |

Description of test methods and methods of measurement:

Determination of Cu abrasion in 10% strength glycerol dispersion (a) Preparation of the glycerol dispersion 153 g of anhydrous glycerol (German Pharmacopeia 7; density=1.26 g/ml) are weighed into a 250 ml polyethylene beaker. 17 g of cleansing agent are carefully mixed into it by means of a spatula. The mixture is then homogenized with a paddle stirrer (diameter 5.2 cm) for 12 minutes at 1,500 rpm.

(b) Method of measurement of abrasion

The abrasion is measured in an abrasion tester disclosed in the following publications: (1) Pfrengle: Fette, Seifen, Anstrichmittel, 63 (5) (1961), pages 445 to 451 "Abrasion und Reinigungskraft von Putzkörpern in Zahnpasten" ("Abrasion and Cleansing Power of Polishing Agents in Toothpastes") (2) A. RENG and F. DANY, Parfümerie und Kosmetik 59 (2) (1978), pages 37 to 45; "Anwendungstechnische Prüfung von Zahnpasten" ("Performance Testing of Toothpastes"). For this purpose, the 6 troughs of the test apparatus were each covered with 20 ml of the homogeneous dispersion. The abrasion produced by six plane-ground nylon brushes on six plane-ground Cu sheets (electrolytic copper) in five hours as a result of 50,000 reciprocating strokes is determined by differential weighing. In calculating the abrasiveness, the means of the values obtained are taken. The abrasion (abrasiveness) is quoted in mg of Cu.

Determination of Cu abrasion of opaque and transparent toothpastes (a) Preparation of the toothpastes
See above description (b) Method of measurement of abrasion
1. Principle An important piece of information concerning the quality of the toothpaste is the abrasiveness, which as a rule is determined by the RDA method and by the copper abrasion method. The values obtained give important information on the cleansing action and abrasive action on the dental enamel and the neck of the tooth. To carry out the test, a suspension is prepared from the toothpaste and glycerol, and the abrasiveness of this mixture is determined with the abrasion tester.

2. Apparatus and reagents
Triple-roll mill (Optimat 1)
Abrasion tester
Analytical balance
Oven
Glycerol, anhydrous, German Pharmacopeia 7 (density=1.26 g/ml),
Toothpastes 3. Method 3.1 Preparation of the paste suspension 75 g of glycerol are stirred into 100 g of the toothpaste, in a porcelain dish, by means of a spatula, and the mixture is then homogenized 4 times on a triple-roll mill. The paste suspension obtained is used for abrasion testing.

3.2 Measurement of abrasion

The determination is carried out in the abrasion tester. Six cleaned, plane-ground, accurately weighed electrolytic copper sheets are placed in the six troughs of the test apparatus. 20 ml of the homogeneous dispersion are then introduced into each. Plane-ground nylon brushes are placed on the Cu sheets. The test is carried out with 50,000 double strokes (requiring about 5 hours). After completion of the determination, the copper sheets are rinsed first with water and then with acetone and are dried in a desiccator. The completely dry Cu sheets are accurately weighed and the weight difference is quoted as the abrasiveness, in mg of Cu. In the evaluation, any outliers are ignored, and the mean of the remaining values is taken.

4. Evaluation

The abrasiveness is quoted in mg of Cu.

Weight of Cu sheet before determination minus weight of Cu sheet after determination=loss of electrolytic copper in mg=abrasiveness. Test of rheological activity of abrasive silicas in a 30% strength dispersion in a 1:1 glycerol/water mixture

| 1. Sample mixes | 60 g of silica |
| --- | --- |
|  | 70 g of anhydrous glycerol, German Pharmacopeia 7, density 1.26 g/ml |
|  | 70 g of distilled water |
|  | 200 g = 30% strength silica dispersion |

2. Method

The abrasive silicas are stirred manually for 1 minute, using a glass rod, into the glycerol/water mixture in a 400 ml beaker (squat form), and the mixture is left to stand for 24 hours, after which the viscosity is measured.

3. Measurement

The viscosity is measured in the same beaker, using the Brookfield RVT viscometer, spindle 5, at various speeds of revolution.

4. Calculation

Scale reading×factor=viscosity in mPa.s Test of rheological activity of thickening silicas in a 15% strength dispersion in a 1:1 glycerol/water mixture

| 1. Sample mix | 30 g of silica |
| --- | --- |
|  | 85 g of anhydrous glycerol, German Pharmacopeia 7, density 1.26 g/ml |
|  | 85 g of distilled H$_2$O |
|  | 200 g = 15% strength silica dispersion |

2. Method

The thickening silica is stirred manually for 1 minute, using a glass rod, into the glycerol/water mixture in a 400 ml beaker (squat form), and the mixture is left to stand for 24 hours, after which the viscosity was measured.

3. Measurement

The viscosity is measured in the same beaker, using the Brookfield RVT viscometer, spindle 5, at various speeds of revolution.

4. Calculation

Scale reading × factor = viscosity in mPa.s.

Determination of viscosity of toothpastes:

(a) Preparation of the toothpastes

See above description (b) Method of measurement of viscosity

Testing the toothpaste viscosity on a Rotoviscometer, plate and cone system

1. Apparatus

Rotovisko from Haake, Karlsruhe, West Germany, with thermostat, measuring head 50, plate-and-cone No. 8012 and 1224.

2. Method

The toothpaste is first brought to 20°–22° C. and a small amount is then applied with the end of a spatula to the plate. The measurement is carried out at speed level 27. After 30 seconds, the scale value is read off the indicator, since after this time an approximately constant value has been reached.

3. Evaluation

From the speed, pointer reading and calibration constant of the plate-and-cone system used, the viscosity of the paste is found from the equation $$V = K \cdot S \cdot U [mPa \cdot s]$$

where
V = viscosity in mPa·s
U = speed level of the Rotovisko
S = scale reading
K = calibration constant of the cone used Determination of the pH of toothpastes (a) Preparation of the toothpastes See above description (b) Method of pH measurement The pH of toothpastes is extremely important since it can greatly affect the stability of a paste. Extremely alkaline and extremely acid pastes are as a rule undesirable, since they may cause bulging and corrosion of the aluminum tubes. Moreover, in the case of medicated toothpastes, the active ingredient may be chemically attacked and decomposed. Pastes having a neutral pH are therefore preferred.

1. Apparatus

Laboratory pH-meter type 26 from Knick, with glass electrode.

2. Method

The glass electrode is dipped into the toothpaste and after about 3 minutes the pH is read directly from the indicator.

Visual methods of assessment of dental-care compositions (a) Assessment of the ribbon stability of a toothpaste 1. Method The toothpaste is packed in an aluminum tube and a ribbon about 5 cm long is then squeezed out onto a glass plate.

2. Assessment

The stability of the ribbon is assessed after 5 minutes. If the paste has inadequate consistency, the ribbon is seen to have spread. Depending on the width of the ribbon being assessed, the stability is rated 1–4.

(b) Assessment of the transparency of a transparent toothpaste

1. Method (a) the paste is squeezed out between 2 glass plates or (b) the paste is applied to a white sheet with black lines.

2. Assessment re (a) The transparency of the paste may be judged very easily, since inadequate quality immediately manifests itself by clouding. Depending on the degree of clouding, the transparency is rated 1–4.

re (b) If the paste has good transparency, the black line is very clearly discernible through the ribbon of toothpaste. If the transparency is less good, the line is more or less blurred. The transparency is rated 1–4.

(c) Assessment of the separation of toothpastes

1. Method

The paste is stored in aluminum tubes for 3 months at 45° C. and thereafter a ribbon about 5 cm long is pressed onto blotting paper.

2. Assessment

If the toothpaste has a tendency to separate, a film of moisture extending from the ribbon is readily visible in the blotting paper. Depending on the width of this film, the separation is rated 1–4.

Notes

The method described should be used as a rule, since in a few cases the separation is so pronounced that a layer of liquid even forms at the tube nozzle.

1ST SERIES OF EXAMPLES

This series of examples is intended to demonstrate that the novel dental-care composition containing the cleansing agents specified therein, which fulfils the double function of thickening and abrasiveness, meets today's market requirements in respect of abrasiveness and consistency of opaque toothpastes, without other additives. Commercial cleansing agents based on silica gels do not exhibit these properties, as demonstrated by the comparative experiments in the 1st series of examples.

The composition of the investigated opaque pastes is described in more detail in Table No. 3 (recipes 1–12).

Table No. 4 shows the results (pH, Cu abrasion, viscosity, ribbon stability and separation) of the measurements carried out on recipes 1–12. It follows from the results that:

Recipes No. 3 and No. 6, according to the invention, containing 25% by weight of cleansing agent B and C respectively, give toothpastes with stable ribbons and with an abrasiveness in the range of 8–13 mg of Cu, which fully conforms to market requirements.

Recipe No. 9 according to the invention, with 25% by weight of the harder cleansing agent D, forms a paste which, without additives, still retains a tendency to flow. However, its abrasiveness, namely 16–18 mg of Cu, conforms to what is generally expected from highly-cleansing toothpastes, for example smoker's toothpastes.

Recipe No. 12, formulated with 25% by weight of commercial cleansing agents, gives a toothpaste which does not form a stable ribbon. Moreover, even at such a high filler content, the abrasiveness, namely 4–6 mg of Cu, is very low.

TABLE No. 3

Opaque dental-care compositions: Double function of cleansing agents. Recipes without additives.

| Recipe | Consecutive No. | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Distilled water | 40.35 | 35.35 | 30.35 | 40.35 | 35.35 | 30.35 | 40.35 | 35.35 | 30.35 | 40.35 | 35.35 | 30.35 |
| Dehydazol A 400 P | 1.00 | → | → | → | → | → | → | → | → | → | → | → |
| Solbrol M-Na | 0.15 | → | → | → | → | → | → | → | → | → | → | → |
| Saccharin-Na | 0.10 | → | → | → | → | → | → | → | → | → | → | → |
| Sorbitol | 40.00 | → | → | → | → | → | → | → | → | → | → | → |
| $TiO_2$ RN56 | 0.40 | → | → | → | → | → | → | → | → | → | → | → |
| Liquid paraffin | 0.50 | → | → | → | → | → | → | → | → | → | → | → |
| Aromatic oil | 0.50 | → | → | → | → | → | → | → | → | → | → | → |
| Texapon K 12 | 2.00 | → | → | → | → | → | → | → | → | → | → | → |
| Silica B | 15.00 | 20.00 | 25.00 | — | — | — | — | — | — | — | — | — |
| Silica C | — | — | — | 15.00 | 20.00 | 25.00 | — | — | — | — | — | — |
| Silica D | — | — | — | — | — | — | 15.00 | 20.00 | 25.00 | — | — | — |
| Silica E | — | — | — | — | — | — | — | — | — | 15.00 | 20.00 | 25.00 |
| Sum: | 100.00 | → | → | → | → | → | → | → | → | → | → | → |

TABLE No. 4

Opaque dental-care compositions: Double function of cleansing agents. Results without additives.

| Recipe/Properties Consecutive No. | pH | Abrasion mg of Cu | Viscosity mPa.s | Ribbon stability | Separation |
|---|---|---|---|---|---|
| 1 | 5.0 | 7–8 | 1,116 | Rating 4 | Rating 1 |
| 4 | 5.2 | 8–9 | 930 | Rating 4 | Rating 1 |
| 7 | 4.8 | 12–15 | 806 | Rating 4 | Rating 1 |
| 10 | 4.1 | 2–3 | too mobile | Rating 4 | Rating 3 |
| 2 | 5.3 | 7–9 | 1,860 | Rating 3 | Rating 1 |
| 5 | 6.2 | 8–11 | 1,736 | Rating 3 | Rating 1 |
| 8 | 5.8 | 13–16 | 1,364 | Rating 4 | Rating 1 |
| 11 | 4.2 | 2–3 | 868 | Rating 4 | Rating 3 |
| 3 | 5.4 | 8–10 | 3,348 | Rating 1 | Rating 1 |
| 6 | 5.8 | 11–13 | 2,914 | Rating 1 | Rating 1 |
| 9 | 5.4 | 16–18 | 2,604 | Rating 3 | Rating 1 |
| 12 | 4.0 | 4–6 | 1,860 | Rating 3 | Rating 1 |

2ND SERIES OF EXAMPLES

This series of examples is intended to show that the dental-care compositions according to the invention, containing the cleansing agents which are specified in more detail in the claims and have a pronounced double function of thickening and abrasiveness, when used together with additives based on polyethylene glycols conform, in the case of transparent toothpastes, to present-day market requirements in respect of abrasiveness, transparency and consistency. Commercial cleansing agents based on silica gel do not exhibit these properties, as demonstrated by the comparative tests in the 2nd series of examples.

The composition of the transparent pastes investigated is described in more detail in Table No. 5 (recipes 1-12).

TABLE No. 5

Transparent dental-care compositions: Double function of cleansing agents. Recipes with additive

| Recipe | Consecutive No. | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Distilled water | 17.95 | 17.95 | 12.95 | 12.95 | 17.95 | 17.95 | 12.95 | 12.95 | 17.95 | 17.95 | 12.95 | 12.95 |
| Blue dye solution | 0.50 | → | → | → | → | → | → | → | → | → | → | → |
| Dehydazol A 400 P | 0.50 | → | → | → | → | → | → | → | → | → | → | → |
| Solbrol M-Na | 0.15 | → | → | → | → | → | → | → | → | → | → | → |
| Saccharin-Na | 0.10 | → | → | → | → | → | → | → | → | → | → | → |
| Glycerol | 60.00 | → | → | → | → | → | → | → | → | → | → | → |
| Polyethylene glycol 400 | 3.50 | — | 3.50 | — | 3.50 | — | 3.50 | — | 3.50 | — | 3.50 | — |
| Polyethylene glycol 1500 | — | 3.50 | — | 3.50 | — | 3.50 | — | 3.50 | — | 3.50 | — | 3.50 |
| Aromatic oil | 1.00 | → | → | → | → | → | → | → | → | → | → | → |
| Texapon K 12 | 1.30 | → | → | → | → | → | → | → | → | → | → | → |
| Silica A | 15.00 | 15.00 | 20.00 | 20.00 | — | — | — | — | — | — | — | — |
| Silica C | — | — | — | — | 15.00 | 15.00 | 20.00 | 20.00 | — | — | — | — |
| Silica E | — | — | — | — | — | — | — | — | 15.00 | 15.00 | 20.00 | 20.00 |
| Sum: | 100.00 | → | → | → | → | → | → | → | → | → | → | → |

TABLE No. 6

Transparent dental-care compositions: Double function of cleansing agents with additive

| Recipe Consecutive No. | pH | Abrasion mg of Cu | Viscosity mPa.s | Ribbon stability | Separation | Transparency |
|---|---|---|---|---|---|---|
| 1 | 7.6 | 16 | 1,100 | Rating 4 | Rating 1 | Rating 2 |
| 5 | 7.8 | 14 | 1,302 | Rating 4 | Rating 1 | Rating 2 |
| 9 | 5.9 | 7 | not measurable | Rating 4 | Rating 4 | Rating 4 |
| 2 | 7.2 | 15 | 1,320 | Rating 3 | Rating 1 | Rating 2 |
| 6 | 7.9 | 12 | 1,612 | Rating 3 | Rating 1 | Rating 2 |
| 10 | 6.0 | 5 | not measurable | Rating 4 | Rating 4 | Rating 4 |
| 3 | 7.5 | 18 | 1,980 | Rating 3 | Rating 1 | Rating 2 |
| 7 | 7.7 | 14 | 2,480 | Rating 2 | Rating 1 | Rating 2 |
| 11 | 5.8 | 6 | 868 | Rating 4 | Rating 1 | Rating 4 |

TABLE No. 6-continued

| Transparent dental-care compositions: Double function of cleansing agents with additive | | | | | | |
|---|---|---|---|---|---|---|
| | | | Results | | | |
| Recipe Consecutive No. | pH | Abrasion mg of Cu | Viscosity mPa.s | Ribbon stability | Separation | Transparency |
| 4 | 7.4 | 17 | 2,980 | Rating 1 | Rating 1 | Rating 2 |
| 8 | 7.7 | 13 | 3,410 | Rating 1 | Rating 1 | Rating 2 |
| 12 | 5.8 | 6 | 1,550 | Rating 3 | Rating 1 | Rating 4 |

Table No. 6 shows the results (pH, Cu abrasion, viscosity, ribbon stability, separation and transparency) of the measurements carried out on recipes 1-12. It follows that:

Recipes No. 4 and No. 8 according to the invention, containing 20% by weight of cleansing agents A and C respectively and 3.5% of polyethylene glycol 1,500, give toothpastes which produce stable ribbons and have an abrasiveness which fully conforms to market requirements.

Recipes No. 11 and No. 12, formulated with 20% by weight of commercial cleansing agents, do not form stable-ribbon toothpastes either with 3.5% of polyethylene glycol 400 or with polyethylene glycol 1,500. The transparency of these pastes is also unsatisfactory.

3RD SERIES OF EXAMPLES

This series of examples is intended to demonstrate that the dental-care composition according to the invention containing the cleansing agents which have the double function of thickening and abrasiveness, together with additives based on polyethylene glycols, conform to present-day market requirements in respect of abrasiveness and consistency and are even superior in respect of the amount of cleansing agent to be employed.

Commercial cleansing agents based on silica gel do not exhibit this property even in the presence of 5% of polyethylene glycol 1,500, as is demonstrated by the comparative tests of the 3rd series of examples.

The composition of the opaque pastes investigated is described in more detail in Table No. 7 (recipes 1-12).

Table No. 8 gives the results (pH, Cu abrasion, viscosity, ribbon stability and separation) of the measurements carried out on recipes 1-12. It follows from these that:

Recipes No. 4, No. 7 and No. 8 according to the invention, containing 20% by weight of cleansing agent A or C and 2% by weight or 5% by weight of polyethylene glycol 1,500, from stable-ribbon toothpastes whose abrasiveness fully conforms to market requirements.

Recipes No. 9, No. 10, No. 11 and No. 12, formulated with 20% by weight of commercial cleansing agents, do not form stable-ribbon toothpastes either with 2% by weight or with 5% by weight of polyethylene glycol 400 or polyethylene glycol 1,500.

TABLE No. 7

| Opaque dental-care compositions: Double function of cleansing agents. Recipes with additive | | | | | | | | | | | | |
|---|---|---|---|---|---|---|---|---|---|---|---|---|
| | Consecutive No. | | | | | | | | | | | |
| Recipe | 1 | 2 | 3 | 4 | 5 | 6 | 7 | 8 | 9 | 10 | 11 | 12 |
| Distilled water | 33.35 | 30.35 | 33.35 | 30.35 | 33.35 | 30.35 | 33.35 | 30.35 | 33.35 | 30.35 | 33.35 | 30.35 |
| Dehydazol A 400P | 1.00 | → | → | → | → | → | → | → | → | → | → | → |
| Solbrol M-Na | 0.15 | → | → | → | → | → | → | → | → | → | → | → |
| Saccharin-Na | 0.10 | → | → | → | → | → | → | → | → | → | → | → |
| Sorbitol | 40.00 | → | → | → | → | → | → | → | → | → | → | → |
| Polyethylene glycol 400 | 2.00 | 5.00 | — | — | 2.00 | 5.00 | — | — | 2.00 | 5.00 | — | — |
| Polyethylene glycol 1500 | — | — | 2.00 | 5.00 | — | — | 2.00 | 5.00 | — | — | 2.00 | 5.00 |
| $TiO_2$ RN 56 | 0.40 | → | → | → | → | → | → | → | → | → | → | → |
| Liquid paraffin | 0.50 | → | → | → | → | → | → | → | → | → | → | → |
| Aromatic oil | 0.50 | → | → | → | → | → | → | → | → | → | → | → |
| Texapon K 12 | 2.00 | → | → | → | → | → | → | → | → | → | → | → |
| Silica A | 20.00 | 20.00 | 20.00 | 20.00 | — | — | — | — | — | — | — | — |
| Silica C | — | — | — | — | 20.00 | 20.00 | 20.00 | 20.00 | — | — | — | — |
| Silica E | — | — | — | — | — | — | — | — | 20.00 | 20.00 | 20.00 | 20.00 |
| Sum: | 100.00 | → | → | → | → | → | → | → | → | → | → | → |

TABLE No. 8

| Opaque dental-care compositions: Double function of cleansing agents with additive. | | | | | |
|---|---|---|---|---|---|
| | | Results | | | |
| Recipe Consecutive No. | pH | Abrasion mg of Cu | Viscosity mPa.s | Ribbon stability | Separation |
| 1 | 5.6 | 13 | 1,860 | Rating 3 | Rating 1 |
| 5 | 5.9 | 12 | 2,348 | Rating 2 | Rating 1 |
| 9 | 4.0 | 5 | 1,040 | Rating 4 | Rating 1 |
| 2 | 5.7 | 12 | 2,120 | Rating 2 | Rating 1 |
| 6 | 5.5 | 10 | 2,506 | Rating 2 | Rating 1 |
| 10 | 4.1 | 4 | 1,320 | Rating 3 | Rating 1 |
| 3 | 5.5 | 15 | 2,450 | Rating 2 | Rating 1 |
| 7 | 5.8 | 12 | 2,640 | Rating 1 | Rating 1 |
| 11 | 4.0 | 6 | 1,220 | Rating 3 | Rating 1 |
| 4 | 5.6 | 14 | 3,120 | Rating 1 | Rating 1 |
| 8 | 5.9 | 13 | 3,320 | Rating 1 | Rating 1 |
| 12 | 4.1 | 6 | 1,580 | Rating 3 | Rating 1 |

4TH SERIES OF EXAMPLES

The series of examples which follows is intended to demonstrate the marked superiority of the cleansing agents used in the dental-care compositions according to the invention, in respect of their abrasion and also of their thickening action, compared to commercial cleansing agents based on silica gels. In order to highlight the differences more clearly, use is made of a thickening precipitated silica, for example FK 320 DS. The test results show that, at a constant degree of filling of 22% by weight, the abrasive action and thickening action in the dental-care composition according to the invention can be varied by the choice of the ratio of abrasive component to thickening component. By comparison, this variability is very greatly restricted when using commercial cleansing agents.

The composition of the opaque toothpastes investigated is described in more detail in Table No. 9 (recipes 1–20).

Table No. 10 contains the results (pH, Cu abrasion and viscosity) of the measurements carried out on recipes 1–20. The conclusion for recipes 1–10 are as follows:

Recipes No. 1–No. 5 according to the invention, having a total silica content of 22% by weight, in every case conform to what the market requires of a dental-care composition. This is also true of those formulations which contain either none, or only 2% by weight, of a thickening precipitated silica (type G). On increasing the content of thickening component while at the same time lowering the content of cleansing agent (type G), the toothpastes obtained give very stable ribbons and, because of their relatively high viscosity, permit savings of thickening silica. In contrast, recipes No. 8–No. 10, tested for comparison and having the same total silica content, but containing cleansing agent type E, are insufficiently viscous. Only with recipes No. 6 and No. 7, which contain 12 and 14% by weight of thickening silica (type G), are toothpastes with an acceptable consistency obtained.

In recipes No. 1–No. 5 according to the invention, and also in comparative recipes No. 6–No. 10, the abrasiveness does not increase linearly with increasing content of cleansing agent type C or type E. However, the increase in abrasiveness, viewed in absolute terms, is greater in the recipes according to the invention, containing cleansing agent of type C, than in the comparative recipes, containing the commercial cleansing agent of type E.

As regards the results, shown in Table No. 10, of the measurements on recipes No. 11–No. 20, the conclusions are:

Recipes No. 11–No. 20 according to the invention, having a total silica content of 22% by weight, substantially conform to what the market requires of a dental-care composition. Formulations No. 14, No. 15, No. 19 and No. 20, which contain none, or only 2% by weight, of a thickening precipitated silica (type G), tend to flow. On increasing the content of thickener component, while at the same time lowering the content of cleansing agent component (types A and D), toothpastes are obtained which give very stable ribbons and whose recipes, because of their relatively high level of thickening, permit savings of thickening silica.

In the cleansing agents according to the invention, of type A and type D, Cu abrasion values in the range of 11–18 mg of Cu can be obtained, made-to-measure, depending on the composition of the recipes in respect of abrasive component and thickening component. Even in the extreme case where only abrasive component is used, the ribbon stability remains good. However, it is found that the Cu abrasion values increase far from linearly with the concentration of the abrasive component while on the other hand the abrasiveness of the dental-care compositions according to the invention can be selected within relatively wide limits without having to sacrifice other important properties of the composition, such as ribbon stability and separation stability. This is not true when using the commercial cleansing agent (type E) based on silica gel.

TABLE No. 9

Opaque dental-care compositions: Double function of cleansing agents.
Recipes contain precipitated silicas having a thickening action.

| Recipe | Consecutive No. | | | | | | | | | |
|---|---|---|---|---|---|---|---|---|---|---|
| | 1 | 2 | 3 | 4 | 5 | 6 | 7 | 8 | 9 | 10 |
| Distilled water | 33.40 | → | → | → | → | → | → | → | → | → |
| Dehydazol A 400P | 1.00 | → | → | → | → | → | → | → | → | → |
| Solbrol M | 0.15 | → | → | → | → | → | → | → | → | → |
| Saccharin-Na | 0.05 | → | → | → | → | → | → | → | → | → |
| Sorbitol | 30.00 | → | → | → | → | → | → | → | → | → |
| Glycerol | 10.00 | → | → | → | → | → | → | → | → | → |
| $TiO_2$ RN 56 | 0.40 | → | → | → | → | → | → | → | → | → |
| Liquid paraffin | 0.50 | → | → | → | → | → | → | → | → | → |
| Aromatic oil | 0.50 | → | → | → | → | → | → | → | → | → |
| Texapon K 12 | 2.00 | → | → | → | → | → | → | → | → | → |
| Silica C | 8.00 | 10.00 | 14.00 | 20.00 | 22.00 | — | — | — | — | — |
| Silica E | — | — | — | — | — | 8.00 | 10.00 | 14.00 | 20.00 | 22.00 |
| Silica G | 14.00 | 12.00 | 8.00 | 2.00 | — | 14.00 | 12.00 | 8.00 | 2.00 | — |
| Sum: | 100.00 | → | → | → | → | → | → | → | → | → |

| Recipe | Consecutive No. | | | | | | | | | |
|---|---|---|---|---|---|---|---|---|---|---|
| | 11 | 12 | 13 | 14 | 15 | 16 | 17 | 18 | 19 | 20 |
| Distilled water | 33.40 | → | → | → | → | → | → | → | → | → |
| Dehydazol A 400P | 1.00 | → | → | → | → | → | → | → | → | → |
| Solbrol M | 0.15 | → | → | → | → | → | → | → | → | → |
| Saccharin-Na | 0.05 | → | → | → | → | → | → | → | → | → |
| Sorbitol | 30.00 | → | → | → | → | → | → | → | → | → |
| Glycerol | 10.00 | → | → | → | → | → | → | → | → | → |
| $TiO_2$ RN 56 | 0.40 | → | → | → | → | → | → | → | → | → |
| Liquid paraffin | 0.50 | → | → | → | → | → | → | → | → | → |
| Aromatic oil | 0.50 | → | → | → | → | → | → | → | → | → |
| Texapon K 12 | 2.00 | → | → | → | → | → | → | → | → | → |
| Silica A | 8.00 | 10.00 | 14.00 | 20.00 | 22.00 | — | — | — | — | — |
| Silica D | — | — | — | — | — | 8.00 | 10.00 | 14.00 | 20.00 | 22.00 |
| Silica G | 14.00 | 12.00 | 8.00 | 2.00 | — | 14.00 | 12.00 | 8.00 | 2.00 | — |
| Sum: | 100.00 | → | → | → | → | → | → | → | → | → |

TABLE No. 10

Opaque dental-care compositions: Double function of cleansing agents. Recipes contain precipitated silicas having a thickening action.
Results

| Recipe Consecutive No. | pH | Abrasion mg of Cu | Viscosity mPa.s | Assessment of ribbon stability |
|---|---|---|---|---|
| 1 | 4.9 | 8–9 | 6,000 | Rating 1 |
| 2 | 5.2 | 9–11 | 5,270 | Rating 1 |
| 3 | 5.3 | 10–12 | 4,650 | Rating 1 |
| 4 | 5.5 | 13–14 | 3,800 | Rating 1 |
| 5 | 5.4 | 13–15 | 3,100 | Rating 1 |
| 6 | 4.4 | 2–3 | 5,200 | Rating 1 |
| 7 | 4.2 | 2–3 | 3,400 | Rating 1 |
| 8 | 4.2 | 3–4 | 2,700 | Rating 2 |
| 9 | 4.1 | 5 | 1,800 | Rating 3 |
| 10 | 4.2 | 5–6 | 1,300 | Rating 4 |
| 11 | 5.0 | 11–13 | 5,952 | Rating 1 |
| 12 | 5.2 | 10–12 | 5,230 | Rating 1 |
| 13 | 5.5 | 12–14 | 4,430 | Rating 1 |
| 14 | 5.0 | 13–15 | 3,100 | Rating 2 |
| 15 | 5.5 | 16–18 | 2,840 | Rating 2 |
| 16 | 5.0 | 12–14 | 5,890 | Rating 1 |
| 17 | 5.0 | 14–16 | 4,960 | Rating 1 |
| 18 | 5.1 | 15–17 | 4,340 | Rating 1 |
| 19 | 5.4 | 16–18 | 2,914 | Rating 2 |
| 20 | 5.0 | 16–18 | 2,790 | Rating 2 |

5TH SERIES OF EXAMPLES

The series of examples which follows is intended to provide experimental proof that the use of a few percent of thickening pyrogenic silica, eg. Aerosil ®200V, in combination with the cleansing agents used in the dental-care compositions according to the invention gives toothpastes which in respect of abrasion and thickening characteristics are entirely comparable with commercial dental-care compositions now on the market.

The series of examples also shows that by the use of pyrogenic silicas, as components which help determine the rheology, the total content of silica filler can be markedly reduced.

The composition of the opaque toothpastes investigated is shown in more detail in Table No. 11 (recipes No. 1–No. 4).

Table No. 12 contains the results (pH, Cu abrasion and viscosity) of the measurements on recipes No. 1–No. 4. It follows from these that:

Using the pyrogenic silica Aerosil ®200V as a thickening silica, the total silica content in an opaque dental-care composition according to the invention can be reduced by 17% by weight if, at the same time, 14% by weight of cleansing agent C and 3% by weight of thickening silica of type H are employed. In that case, the characteristics of a commercial opaque toothpaste, in respect of abrasion and rheological properties, are obtained.

TABLE No. 11

Opaque dental-care compositions: Double function of cleansing agents. Recipes contain pyrogenic silica having a thickening action.

| Recipe | Consecutive No. | | | |
|---|---|---|---|---|
| | 1 | 2 | 3 | 4 |
| Distilled water | 35.35 | 37.35 | 38.35 | 38.35 |
| Dehydazol A 400 P | 1.00 | → | → | → |
| Solbrol M | 0.15 | → | → | → |
| Saccharin | 0.10 | → | → | → |
| Sorbitol | 40.00 | → | → | → |
| TiO₂ RN 56 | 0.40 | → | → | → |
| Liquid paraffin | 0.50 | → | → | → |
| Aromatic oil | 0.50 | → | → | → |
| Texapon K 12 | 2.00 | → | → | → |
| Silica C | 18.00 | 16.00 | 15.00 | 14.00 |

TABLE No. 11-continued

Opaque dental-care compositions: Double function of cleansing agents. Recipes contain pyrogenic silica having a thickening action.

| Recipe | Consecutive No. | | | |
|---|---|---|---|---|
| | 1 | 2 | 3 | 4 |
| Silica H | 2.00 | 2.00 | 2.00 | 3.00 |
| Sum | 100. | → | → | → |

TABLE No. 12

Opaque dental-care compositions: Double function of cleansing agents. Recipes contain pyrogenic silica having a thickening action.
Results

| Recipe Consecutive No. | pH | Abrasion mg of Cu | Viscosity mPa.s | Assessment of ribbon stability |
|---|---|---|---|---|
| 1 | 5.4 | 10–11 | 2,420 | Rating 2 |
| 2 | 5.2 | 9–10 | 2,170 | Rating 3 |
| 3 | 5.4 | 9–10 | 1,800 | Rating 3 |
| 4 | 5.0 | 8–10 | 2,728 | Rating 1 |

6TH SERIES OF EXAMPLES

This series of examples serves to show the superiority of the novel dental-care composition, in respect of shelf life, in comparison with the commercial toothpastes wherein the cleaning agents are based on silica xerogels, chalk and phosphate derivatives.

The examples are intended to demonstrate the very important property of shelf life in respect of the variation of rheological properties with time (after-thickening is a phenomenon to be feared) and also in respect of the dependence of abrasiveness on time.

The opaque and transparent toothpastes prepared for the storage tests, as well as the chalk and phosphate toothpastes considered for comparative purposes are shown, in respect of their composition, in Tables No. 13–No. 16.

The results of the shelf life test, which extended over 12 months, are summarized, for all the systems investigated, in Tables No. 17–No. 20.

TABLE No. 13

Opaque dental-care compositions (containing silica). Recipes for testing the shelf life.

| Recipe | Consecutive No. | | | | | |
|---|---|---|---|---|---|---|
| | 1 | 2 | 3 | 4 | 5 | 6 |
| Distilled water | 35.35 | → | → | → | → | → |
| Dehydazol A 400 P | 1.00 | → | → | → | → | → |
| Solbrol M | 0.15 | → | → | → | → | → |
| Saccharin | 0.10 | → | → | → | → | → |
| Sorbitol | 40.00 | → | → | → | → | → |
| TiO₂ RN 56 | 0.40 | → | → | → | → | → |
| Liquid paraffin | 0.50 | → | → | → | → | → |
| Aromatic oil | 0.50 | → | → | → | → | → |
| Texapon K 12 | 2.00 | → | → | → | → | → |
| Silica A | 10.00 | — | — | — | — | — |
| Silica B | — | 10.00 | — | — | — | — |
| Silica C | — | — | 10.00 | — | — | — |
| Silica D | — | — | — | 10.00 | — | — |
| Silica E | — | — | — | — | 10.00 | — |
| Silica F | — | — | — | — | — | 10.00 |
| Silica G | 10.00 | → | → | → | → | → |
| Sum: | 100.00 | → | → | → | → | → |

TABLE No. 14

Transparent dental-care compositions (containing silica). Recipes for testing the shelf life.

| Recipe | Consecutive No. | | | | |
|---|---|---|---|---|---|
| | 1 | 2 | 3 | 4 | 5 |
| Distilled water | 12.95 | → | → | → | → |

TABLE No. 14-continued

Transparent dental-care compositions (containing silica).
Recipes for testing the shelf life.

| Recipe | Consecutive No. | | | | |
|---|---|---|---|---|---|
| | 1 | 2 | 3 | 4 | 5 |
| Dehydazol A 400 P | 0.50 | → | → | → | → |
| Solbrol M—Na | 0.15 | → | → | → | → |
| 0.5% dye solution | 0.50 | → | → | → | → |
| Saccharin-Na | 0.10 | → | → | → | → |
| Glycerol | 60.00 | → | → | → | → |
| Polyethylene glycol 400 | 3.50 | → | → | → | → |
| Aromatic oil | 1.00 | → | → | → | → |
| Texapon K 12 | 1.30 | → | → | → | → |
| Silica A | 10.00 | — | — | — | — |
| Silica C | — | 10.00 | — | — | — |
| Silica D | — | — | 10.00 | — | — |
| Silica E | — | — | — | 10.00 | — |
| Silica F | — | — | — | — | 10.00 |
| Silica G | 10.00 | → | → | → | → |
| Sum | 100.00 | → | → | → | → |

TABLE No. 15

Dental-care composition based on chalk.
Recipe for testing the shelf life.

| Recipe | Consecutive No. 1 |
|---|---|
| Distilled water | 41.05 |
| Dehydazol A 400 P | 1.00 |
| Solbrol M | 0.15 |
| Saccharin | 0.25 |
| Glycerol | 20.00 |
| Aromatic oil | 1.75 |
| Texapon K 12 | 4.00 |
| Chalk | 29.80 |
| Silica H | 2.00 |
| Sum: | 100.00 |

TABLE No. 16

Dental-care composition based on dicalcium phosphate
dihydrate. Recipe for testing the shelf life.

| Recipe | Consecutive No. 1 |
|---|---|
| Distilled water | 29.00 |
| Dehydazol A 400 P | 0.80 |
| Solbrol M-Na | 0.15 |
| Saccharin-Na | 0.05 |
| Sorbitol | 20.00 |
| Glycerol | 5.00 |
| Aromatic oil | 0.50 |
| Texapon K 12 | 2.00 |
| Dicalcium phosphate dihydrate (Dentphos) | 41.00 |
| Silica H | 1.50 |
| Sum: | 100.00 |

TABLE NO. 17

Opaque silica-containing dental-care composition. Shelf life results

| Recipe Consecutive No. | Properties | Storage time: | | | | | |
|---|---|---|---|---|---|---|---|
| | | immediate | 1 month | 3 months | 6 months | 9 months | 12 months |
| 1 | Abrasion (mg of Cu) | 13 | 12 | 12 | 12 | 12 | 13 |
| | Viscosity (mPa.s) | 10,100 | 9,600 | 10,300 | 10,500 | 10,750 | 10,900 |
| 2 | Abrasion (mg of Cu) | 5 | 6 | 7 | | | |
| | Viscosity (mPa.s) | 12,240 | 11,850 | 10,500 | | | |
| 3 | Abrasion (mg of Cu) | 11 | 10 | 9 | | | |
| | Viscosity (mPa.s) | 11,016 | 10,890 | 10,240 | | | |
| 4 | Abrasion (mg of Cu) | 13 | 14 | 12 | | | |
| | Viscosity (mPa.s) | 9,180 | 9,220 | 10,100 | | | |
| 5 | Abrasion (mg of Cu) | 3 | 4 | 5 | 5 | 7 | 8 |
| | Viscosity (mPa.s) | 9,400 | 6,800 | 5,500 | 4,800 | 3,950 | 2,800 |
| 6 | Abrasion (mg of Cu) | 6 | 7 | 8 | 8 | 9 | 11 |
| | Viscosity (mPa.s) | 8,600 | 7,100 | 6,500 | 5,800 | 3,500 | 2,170 |

TABLE NO. 18

Transparent silica-containing dental-care composition. Shelf life results

| Recipe Consecutive No. | Properties | Storage time: | | | | | |
|---|---|---|---|---|---|---|---|
| | | immediate | 1 month | 3 months | 6 months | 9 months | 12 months |
| 1 | Abrasion (mg of Cu) | 12 | 13 | 13 | 14 | 12 | 14 |
| | Viscosity (mPa.s) | 10,000 | 9,800 | 9,500 | 10,200 | 10,500 | 10,100 |
| 2 | Abrasion (mg of Cu) | 12 | 11 | 13 | | | |
| | Viscosity (mPa.s) | 12,900 | 12,500 | 11,500 | | | |
| 3 | Abrasion (mg of Cu) | 14 | 13 | 12 | | | |
| | Viscosity (mPa.s) | 11,300 | 10,800 | 11,200 | | | |
| 4 | Abrasion (mg of Cu) | 6 | 6 | 6 | 10 | 11 | 12 |
| | Viscosity (mPa.s) | 9,800 | 7,800 | 7,500 | 4,900 | 3,900 | 2,800 |
| 5 | Abrasion (mg of Cu) | 12 | 16 | 17 | 17 | 19 | 20 |
| | Viscosity (mPa.s) | 9,800 | 8,500 | 6,300 | 4,700 | 2,950 | 2,300 |

TABLE NO. 19

Dental-care composition based on chalk. Shelf life results

| Recipe Consecutive No. | Properties | Storage time: | | | | | |
|---|---|---|---|---|---|---|---|
| | | immediate | 1 month | 3 months | 6 months | 9 months | 12 months |
| 1 | Abrasion (mg of Cu) | 8 | 9 | 10 | 10 | 9 | 8 |
| | Viscosity (mPa.s) | 6,450 | 6,800 | 4,200 | 4,500 | 3,900 | 3,600 |

TABLE NO. 20

Dental-care composition based on dicalcium phosphate dihydrate. Shelf life results

| Recipe Consecutive No. | Properties | Storage time: immediate | 1 month | 3 months | 6 months | 9 months | 12 months |
|---|---|---|---|---|---|---|---|
| 1 | Abrasion (mg of Cu) | 3 | 3 | 4 | 3 | 2 | 3 |
|   | Viscosity (mPa.s) | 9,350 | 9,100 | 8,150 | 6,350 | 4,050 | 3,000 |

The following relationships can be demonstrated:

The dental-care compositions according to the invention (see Table No. 17, recipes No. 1–No. 4 and Table No. 18, recipes No. 1–No. 3), which contain, respectively, cleansing agents A, B, C and D and cleansing agents A, C and D, surprisingly show an exceptional shelf life. This is true both of the abrasiveness and the viscosity characteristics in opaque and in transparent toothpastes. In practical terms, this result means that the abrasiveness determined at the final quality control of the product also applies after the product has been stored by the consumer, and that neither does the greatly feared after-thickening occur, causing the toothpaste to be unusable by the consumer, nor does diminishing viscosity cause the requisite ribbon stability to disappear and bring about the disliked phenomenon of separation.

The dental-care compositions which are employed for comparison and which contain the commercial cleansing agents E and F, based on silica gel (see Table No. 17, recipe No. 5 and No. 6, and Table No. 18, recipe No. 4 and No. 5) show after one year's storage, both in the case of opaque and of transparent systems, a great increase in abrasiveness (80–165%?) and a great decrease in initial viscosity (down to 23%), which markedly lower the quality of these dental-care compositions. Accordingly, such compositions are not storage-stable over the chosen period of investigation.

The dental-care compositions, also employed for comparative purposes, which contain chalk or dicalcium phosphate dihydrate as commercial cleansing agents (cf. Tables No. 19 and No. 20) admittedly retain their abrasiveness over a period of one year's storage, but in these systems again, a marked decrease of the initial viscosity is observed, this being somewhat more pronounced (down to 32%) in phosphate-containing pastes than in chalk-containing pastes (down to 56%). Accordingly, these dental-care compositions can also not be regarded as storage-stable over the chosen period of investigation.

The patents and patent applications identified above are relied on and incorporated herein by reference.

We claim:

1. A transparent dental-care toothpaste composition having a smooth, speck-free and glossy ribbon as well as improved shelf life in respect of rheology and abrasiveness, which comprises a sufficient amount of water, an abrasive agent which is a precipitated silica characterized by the following physicochemical properties:

| | | |
|---|---|---|
| BET surface area determined according to DIN 66,131 | m²/g | 15–110 |
| Tamped density | g/l | 150–750 |
| Secondary particle size distribution curve according to Coulter counter | | according to FIG. 1 |
| "ALPINE" screen retainings >63 μm | % by weight | <1.5 |
| Cu abrasion in 10% strength glycerol dispersion | mg | 5–30 |
| Viscosity of a 30% strength dispersion in a 1:1 water/glycerol mixture (Brookfield RTV Sp 5) | mPa.s | 30,000–60,000 |
| Lightness value A according to DIN 55,921 | % | 86–96 | and an additional precipitated silica.

2. A transparent dental-care toothpaste composition having a smooth, speck-free and glossy ribbon as well as improved shelf life in respect of rheology and abrasiveness, which comprises a sufficient amount of water, a precipitated silica thickening agent and an abrasive agent which is a precipitated silica characterized by the following physico-chemical properties:

| | | |
|---|---|---|
| BET surface area determined according to DIN 66,131 | m²/g | 15–110 |
| Tamped density | g/l | 150–750 |
| Secondary particle size distribution curve according to Coulter counter | | according to FIG. 1 |
| "ALPINE" screen retainings >63 μm | % by weight | <1.5 |
| Cu abrasion in 10% strength glycerol dispersion | mg | 5–30 |
| Viscosity of a 30% strength dispersion in a 1:1 water/glycerol mixture (Brookfield RTV Sp 5) | mPa.s | 30,000–60,000 |
| Lightness value A according to DIN 55,921 | % | 86–96 | wherein said precipitated silica abrasive agent is prepared by providing an initial alkali metal silicate solution having a concentration of about 5–25 g of $SiO_2$ per liter of solution and adding thereto an acid and alkali metal silicate solution of particular concentrations, at particular feed rates, while maintaining a precipitation temperature in the reaction medium between 80° and 90° C., the precipitation being carried out under such conditions that the viscosity of the reaction medium is kept, for at least 30% of the total precipitation time, at a uniform low value while the pH is kept between 10 and 12, and the addition of the reactants only being terminated when the viscosity, after passing through a maximum, has dropped to a value which is less than 100% above the initial value to obtain an initial suspension of precipitated silica, thereafter diluting the initial suspension of precipitated silica with hot water to provide a precipitated silica content of 10–30 g/l and a sodium sulfate content of 6–20 g/l the temperature being maintained at 85°–95° C., the pH being brought to 7–9 with the addition of sulfuric acid and while keeping the pH value constant, adding alkali metal silicate solution, sulfuric acid and hot water simultaneously over a precipitation period of 30–180 minutes to give a final concentration of precipitated silica of 40–80 g/l, the suspension being then acified with concentrated sulfuric acid to a pH below 7, separating the precipitated silica from the suspension by means of a filter press, washing, drying and thereafter milling with a pendulum roller mill.

3. A transparent dental-care toothpaste composition having a smooth, speck free and glossy ribbon as well as improved shelf life in respect of rheology and abrasiveness, which comprises a sufficient amount of water, an abrasive agent which is a sufficient amount of a precipitated silica characterized by the following physicochemical properties:

| | | |
|---|---|---|
| BET surface area determined according to DIN 66,131 | m²/g | 15–110 |
| Tamped density | g/l | 90–650 |
| Secondary particle size distribution curve according to Coulter counter | according to FIG. 2 | |
| "ALPINE" screen retainings >63 μm | % by weight | <0.1 |
| Cu abrasion in 10% strength glycerol dispersion | mg | 5–30 |
| Viscosity of a 30% strength dispersion in a 1:1 water/glycerol mixture (Brookfield RTV Sp 5) | mPa · s | 30,000–60,000 |
| Lightness value A according to DIN 55,921 | % | 90–96 |

4. A transparent dental-care toothpaste composition having a smooth, speck free and glossy ribbon as well as improved shelf life in respect of rheology and abrasiveness, which comprises a sufficient amount of water, a precipitated silica thickening agent, an abrasive agent which is a sufficient amount of a precipitated silica characterized by the following physicochemical properties:

| | | |
|---|---|---|
| BET surface area determined according to DIN 66,131 | m²/g | 15–110 |
| Tamped density | g/l | 90–650 |
| Secondary particle size distribution curve according to Coulter counter | according to FIG. 2 | |
| "ALPINE" screen retainings >63 μm | % by weight | <0.1 |
| Cu abrasion in 10% strength glycerol dispersion | mg | 5–30 |
| Viscosity of a 30% strength dispersion in a 1:1 water/glycerol mixture (Brookfield RTV Sp 5) | mPa · s | 30,000–60,000 |
| Lightness value A according to DIN 55,921 | % | 90–96 | wherein said precipitated silica is prepared by providing an initial alkali metal silicate solution having a concentration of about 5–25 g of SiO₂ per liter of solution and adding thereto an acid and alkali metal silicate solution while maintaining a precipitation temperature in the reaction medium between 80° and 90° C., the precipitation being carried out under such conditions that the pH is kept between 10 and 12, the viscosity of the reaction medium being at a uniform low value for at least 30% of the total precipitation time, and terminating the addition of the reactants when the viscosity of the reaction medium, after passing through a maximum, falls to a value which is less than 100% above the initial value to thereby obtain a silica suspension, thereafter diluting the suspension of precipitated silica with hot water to form a precipitated silica content of 10–30 g/l and a sodium sulfate content of 6 to 20 g/l, heating to a temperature of 85°–95°, acidifying with the addition of sulfuric acid to a pH value of 7 to 9, and while keeping the pH value constant, adding alkali metal silicate solution, sulfuric acid and hot water simultaneously over a precipitation period of 30–180 minutes to provide a final concentration of precipitated silica of 40–80 g/l, acidifying the suspension with concentrated sulfuric acid to a pH below 7, thereafter separating the precipitated silica from the suspension by a filter press, washing, drying and milling with a jet mill.

5. The composition of claim 1, wherein said precipitated silica comprising about 15 to 20% by weight of the composition.

6. The composition of claim 3, wherein said precipitated silica comprising about 15 to 20% by weight of the composition.

7. A transparent dental-care toothpaste composition having improved shelf life as set forth in claim 1 which additionally contains glycerol.

8. A transparent dental-care toothpaste composition having improved shelf life as set forth in claim 3 which additionally contains glycerol.

9. The transparent dental-care composition as set forth in claim 1 which contains at least one of the group consisting of a binder, a preservative, a sweetener, an aromatic oil, a foaming agent, a fluoride and a dye.

10. The transparent dental-care composition as set forth in claim 3 which contains at least one of the group consisting of a binder, a preservative, a sweetener, an aromatic oil, a foaming agent, a fluoride and a dye.

11. A transparent dental-care toothpaste composition according to claim 1 which additionally comprises blue dye solution, carboxymethylcellulose, sodium salt of methyl p-hydroxybenzoate, saccharin, glycerol, polyethyleneglycol, an aromatic oil and sodium lauryl sulfate.

12. A transparent dental-care toothpaste composition according to claim 3 which additionally comprises blue dye solution, carboxymethylcellulose, sodium salt of methyl p-hydroxybenzoate, saccharin, glycerol, polyethyleneglycol, an aromatic oil and sodium lauryl sulfate.

13. A transparent dental-care toothpaste composition for smokers according to claim 3 wherein the precipitated silica abrasive agent has the following characteristics:

| | | |
|---|---|---|
| BET surface area determined according to DIN 66,131 | m²/g | 15–110 |
| Tamped density | g/l | 90–650 |
| Secondary particle size distribution curve according to Coulter counter | according to FIG. 2 | |
| "ALPINE" screen retainings >63 μm | % by weight | <0.1 |
| Cu abrasion in 10% strength glycerol dispersion | mg | 16–18 |
| Viscosity of a 30% strength dispersion in a 1:1 water/glycerol mixture (Brookfield RTV Sp 5) | mPa · s | 30,000–60,000. |

14. A transparent dental-care toothpaste composition as set forth in claim 1, wherein the abrasive silica has a BET surface area 103 m²/g and an ALPINE screen retainings of 1.4% by weight, a Cu abrasion of 14, a viscosity of 36,000, and a lightness value of 94.4, wherein the viscosity is determined in 15% strength dispersion in a 1:1 glycerol/water mixture.

15. A transparent dental-care toothpaste composition according to claim 1, wherein the silica has a BET surface area of 70 m²/g, an ALPINE screen retainings of 0.1% by weight, a Cu abrasion of 12, a viscosity of 38,400 and a lightness value of 95.7.

16. A transparent dental-care toothpaste composition according to claim 1, wherein the silica has a BET surface area of 101 $m^2/g$, an ALPINE screen retainings of 0.1% by weight, a Cu abrasion of 8 and a lightness value of 96.8.

17. The dental-care composition according to claim 1, wherein the abrasive silica has a BET surface area of 51 $m^2/g$, an ALPINE screen retainings of 0.1% by weight, a Cu abrasion of 17, a viscosity of 33,500 and a lightness value of 94.6.

18. The transparent dental-care toothpaste composition according to claim 1 which additionally comprises polyethyleneglycol 400.

19. The transparent dental-care toothpaste composition according to claim 1 which additionally comprises polythyleneglycol 1500.

* * * * *